United States Patent [19]

Esquivel H.

[11] Patent Number: 5,059,024
[45] Date of Patent: Oct. 22, 1991

[54] TRISTIMULUS COLOR EVALUATION SAMPLE CUP

[75] Inventor: J. Benjamin Esquivel H., Midland, Mich.

[73] Assignee: The Dow Chemical Company, Midland, Mich.

[21] Appl. No.: 504,521

[22] Filed: Apr. 4, 1990

[51] Int. Cl.[5] .......................... G01N 21/03; G01J 3/46
[52] U.S. Cl. ..................................... 356/246; 356/402
[58] Field of Search ............... 356/244, 245, 246, 402, 356/405, 406, 236; 250/228

[56] References Cited

U.S. PATENT DOCUMENTS

| | | | |
|---|---|---|---|
| 2,483,452 | 10/1949 | Berkley . | |
| 3,869,213 | 3/1975 | Greene | 356/244 |
| 3,956,201 | 5/1976 | Seiner | 356/236 X |
| 3,999,860 | 12/1976 | Demsky et al. | 356/244 |
| 4,249,826 | 2/1981 | Studievic et al. | 356/244 |
| 4,658,131 | 4/1987 | Stark | 250/228 |

Primary Examiner—Vincent P. McGraw
Attorney, Agent, or Firm—Timothy S. Stevens

[57] ABSTRACT

An improved tristimulus sample cup of the type that generally includes an optically transparent bottom portion, a side wall portion and an open mouth. Such cups have a cavity for holding the sample, the cavity being defined by the bottom and side portions of the cup. The side wall portion has a surface which is exposed to the cavity. The improvement of the present invention relates to the optical properties of this surface of the side wall portion of the cup which is exposed to the cavity, i.e., that it have a diffuse reflectance at 580 nanometers of preferably more than eighty percent. In addition, if the sample cup is equipped with a plunger positioned in the mouth of the cup, the plunger having a surface exposed to the cavity, then the plunger surface exposed to the cavity should also have a diffuse reflectance at 580 nanometers of preferably more than eighty percent. A highly preferred cup of the present invention is made with a flat optical glass bottom, sides of white TEFLON . brand PTFE and a plunger of white TEFLON brand PTFE. The primary benefit of the present invention is improved color sensitivity and precision when a somewhat translucent, lightly colored granular or pelletized sample is analyzed.

14 Claims, 1 Drawing Sheet

TRISTIMULUS COLOR EVALUATION SAMPLE CUP

FIELD OF THE INVENTION

The invention is in the field of color analysis and more specifically the invention is in the field of sample cups used in tristimulus color analysis of granular samples.

BACKGROUND OF THE INVENTION

The measurement of color is of great importance in the quality control of many critical intermediates and finished products. Color is not just a physical phenomenon, it is also perception, and perception can not be measured. However, the physical properties involved in the preception of color such as the spectral response of the observer, the reflectance or transmission curves of the sample, and the characteristics of the illuminating source, all can be measured and standardized. Tristimulus colorimetry is an instrumental technique used to assess those characteristics of transmitted or reflected light according to three spectral functions. The theoretical background for this technique was established by the International Commission on Illumination in 1931. The theory, practice and application of tristimulus colorimetry can be surveyed by reference to the following texts: F. Billmeyer and M. Saltzman *Principles of Color Technology* 1981; R. Johnston and M. Saltzman *Industrial Color Technology* 1971; and D. Judd and G. Wyszecki *Color in Business, Science and Industry* 1975.

Tristimulus colorimeters normally employ reflection techniques to measure the color of solid samples. Two optical designs are predominant in this type of instrumentation. One employs an integrating sphere to diffusively illuminate the sample and measure its reflectance curve. Sphere instruments usually include a scanning grating or photodiode array spectral analyzer. A second instrumental design relies on an angular illumination/observation geometry, commonly 45 degree illumination and 0 degree observation. These units use either grating or filter analyzers.

A large perfectly homogeneous, and opaque solid would be close to the ideal type of specimen for color evaluation when contrasted with pelletized or granulated materials. Those nearly ideal solids are easily handled, do not require any sampling device, and yield very precise results. In contrast, pelletized or granulated samples require some type of sample container. Typically, the sample container has a flat optical glass bottom, glass sides and an open mouth at the top. The granular or pelletized sample is poured into the cup and held in place with a plunger inserted into the mouth of the cup. The cup is then placed over the illumination/observation aperture of the tristimulus instrument so that light can be shown through the flat optical glass bottom of the cup, illuminate the sample in the cup and then be reflected back into the instrument for tristimulus analysis. A black cover is usually placed over the sample cup to keep room light from finding its way into the instrument when a sample is being analyzed. If the granular or pelletized sample is translucent and lightly colored, then the use of a conventional sample cup results in poor precision and poor color sensitivity.

SUMMARY OF THE INVENTION

The present invention is specifically applicable to the tristimulus color evaluation of granular or pelletized samples that are somewhat translucent and lightly colored so that better precision and color sensitivity may be obtained. The present invention is an improvement of conventional tristimulus sample cups which generally include an optically transparent bottom portion, a side wall portion and an open mouth. These cups have a cavity for holding the sample, the cavity being defined by the bottom and side portions of the cup. The improvement of the present invention relates to the optical properties of the surface of the side wall portion of the cup which is exposed to the cavity, i.e., that it has a diffuse reflectance at 580 nanometers of more than twenty percent. In addition, if the sample cup is equipped with a plunger positioned in the mouth of the cup, the plunger having a surface exposed to the cavity, then the plunger surface exposed to the cavity should also have a diffuse reflectance at 580 nanometers of more than twenty percent. A highly preferred cup of the present invention is made with a flat optical glass bottom, sides of TEFLON brand PTFE and a plunger of TEFLON brand PTFE.

DETAILED DESCRIPTION OF THE INVENTION

Figure 1:
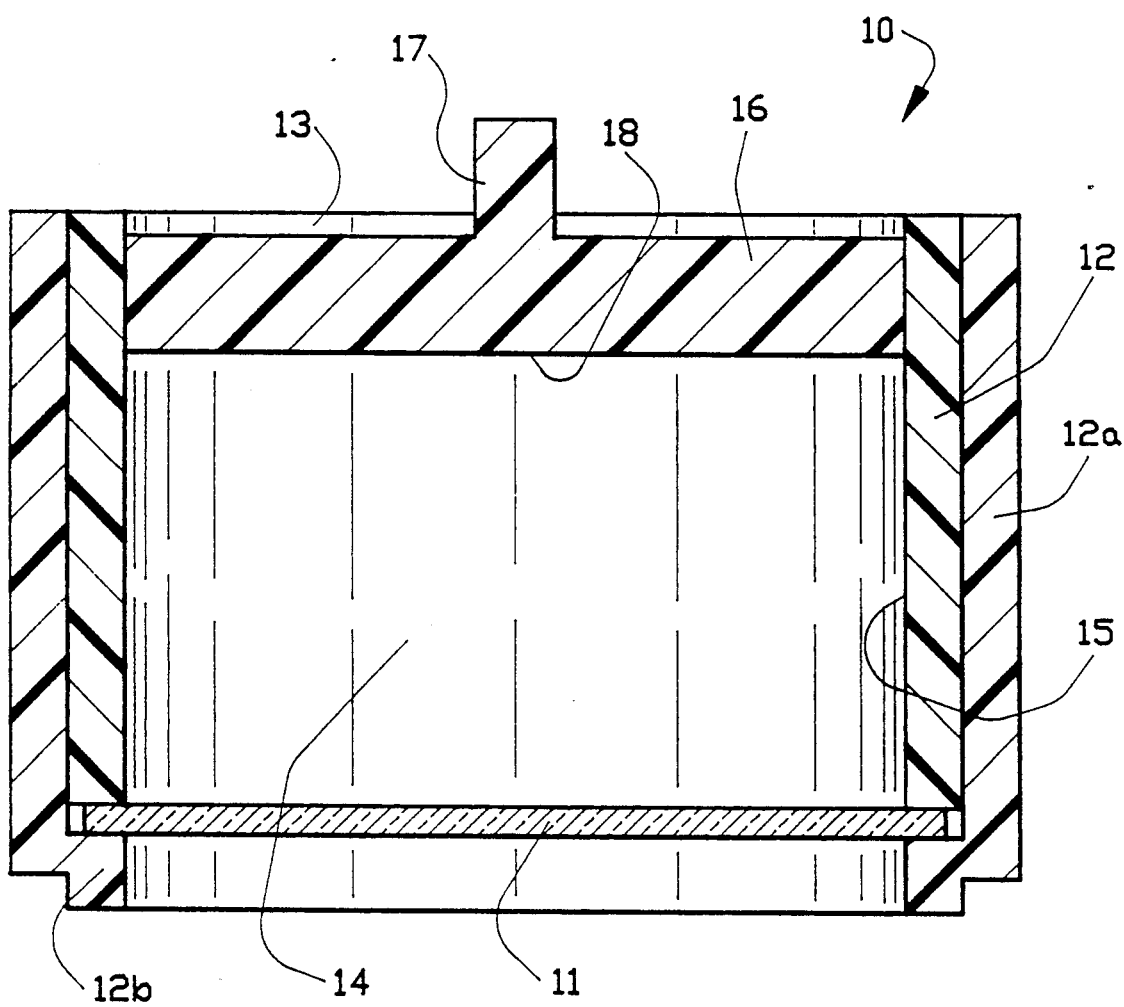
FIG. 1 is a cross sectional side view of a highly preferred embodiment of the present invention.

Referring now to FIG. 1, therein is shown a cross sectional side view of an improved tristimulus sample cup 10 according to the present invention. The bottom portion 11 of the cup 10 is a flat sixty millimeter diameter, two millimeter thick disk of optical glass. The side portion 12 of the cup 10 is a sixty two millimeter outside diameter, fifty four millimeter inside diameter, forty three millimeter tall tube of Teflon brand plastic. The side portion 12 fits within a tubular body 12a which is machined from a seventy millimeter outside diameter, sixty two millimeter inside diameter, forty eight millimeter tall tube of TEFLON brand PTFE. The body 12a is bored to have an inside diameter of sixty two millimeters to accept the side portion 12 and retain the bottom portion 11. An additional advantage of the cup 10 is that it is easily disassembled for cleaning and maintenance. The body 12a is also machined to have a lip 12b to fit into the illumination/observation aperture of a Pacific Scientific series 1000 Colorgard Tristimulus Colorimeter (Silver Spring MD). The cup 10 has an open mouth 13 at the top of the cup 10. The bottom portion 11 and the side portion 12 of the cup 10 define a cavity 14 into which a granular or pelletized sample can be placed. The side portion 12 of the cup 10 has a surface 15 exposed to the cavity 14. The term exposed as used herein and in the claims means visually or optically exposed to light within the cavity 14. The surface 15 has a diffuse reflectance of: about eighty three percent at seven hundred and eighty nanometers; about ninety one percent at five hundred and eighty nanometers; and about ninety nine percent at three hundred and eighty nanometers.

A plunger 16 is positioned in the mouth 13 of the cup 10. The plunger 16 has a handle 17 for manipulating the plunger 16. When the cup 10 is prepared for a tristimulus color evaluation of a granular or pelletized sample, the cavity 14 is filled with the sample, then the plunger 17 is positioned in the mouth 13 of the cup 10 and then the plunger 16 is pushed down against the sample. The plunger 16, the side portion 12 and the body 12a are thick enough to be opaque. Therefore, no cover is needed over them to keep room light from entering the tristimulus instrument when a sample is being analyzed. The plunger 16 is a fifty four millimeter diameter, eight millimeter thick disk of Teflon brand plastic. The plunger 16 has a surface 18 exposed to the cavity 14 when the plunger 16 is positioned in the mouth 13 of the cup 10. The term exposed as used herein and in the claims means visually or optically exposed to light within the cavity 14. The surface 18 has a diffuse reflectance of: eighty three percent at seven hundred and eighty nanometers; ninety one percent at five hundred and eighty nanometers; and ninety nine percent at three hundred and eighty nanometers.

It is critical in the present invention that the surface 15 have a diffuse reflectance at five hundred and eighty nanometers of more than twenty percent, preferably more than forty percent, more preferably more than sixty percent, even more preferably more than eighty percent and most preferably more than ninety percent. Most preferably, the diffuse reflectance of the surface 15 is the same at seven hundred and eighty nanometers, five hundred and eighty nanometers and three hundred and eighty nanometers and at all wavelengths between seven hundred and eighty nanometers and three hundred and eighty nanometers.

When a plunger 16 is used in the present invention, it is critical that the surface 18 have a diffuse reflectance at five hundred and eighty nanometers of more than twenty percent, preferably more than forty percent, more preferably more than sixty percent, even more preferably more that eighty percent and most preferably more than ninety percent. Most preferably, the diffuse reflectance of the surface 18 is the same at seven hundred and eighty nanometers, five hundred and eighty nanometers and three hundred and eighty nanometers and at all wavelengths between seven hundred and eighty nanometers and three hundred and eighty nanometers.

The cup 10 of FIG. 1 is specifically adapted to be used with a Pacific Scientific (Silver Spring, MD) series 1000 Colorgard Tristimulus Colorimeter fitted with a series 05 optical sensor to obtain color readings based on the International Commission on Illumination 1931 standard observer. A conventional Pacific Scientific sample cup can be retrofitted to a sample cup according to the present invention by making a sleeve and plunger, similar to the side portion 12 and plunger 16 of FIG. 1, of appropriate material, such as Teflon brand plastic, and inserting the sleeve and plunger into the cup.

It should be understood that TEFLON brand PTFE is but one example of the many materials that can be used in the present invention. TEFLON brand PTFE may not be the best material. A product known as Halon brand plastic, available from the Diano Corporation of Woburn Mass., may be even better since it is specified according to its white color. It should be possible to use many other plastic materials as well as many ceramic materials. It is also probably possible to line a conventional sample cup with a suitable paper or coat it with a suitable paint. Thus, the material used in the present invention in this regard is not critical as long as it has the necessary above mentioned diffuse reflectance properties.

What is claimed is:

1. An improved tristimulus sample cup generally comprising an optically transparent bottom portion, a side wall portion and an open mouth top, the bottom portion and the side wall portion defining a cavity suitable for holding a granular or pelletized sample within the cavity, the side wall portion having a surface exposed to cavity, wherein the improvement comprises that the side wall surface exposed to the cavity has a diffuse reflectance at 580 nanometers of more than twenty percent.

2. The sample cup of claim 1, wherein the side wall surface exposed to the cavity has a diffuse reflectance at 580 nanometers of more than forty percent.

3. The sample cup of claim 2, wherein the side wall surface exposed to the cavity has a diffuse reflectance at 580 nanometers of more than sixty percent.

4. The sample cup of claim 3, wherein the side wall surface exposed to the cavity has a diffuse reflectance at 580 nanometers of more than eighty percent.

5. The sample cup of claim 4, wherein the side wall surface exposed to the cavity has a diffuse reflectance at 580 nanometers of more than ninety percent.

6. The sample cup of claim 4, wherein the side wall is also opaque.

7. The sample cup of claim 6, wherein the side wall is made of TEFLON brand PTFE and the bottom is made of flat optical glass.

8. The sample cup of claim 1, further comprising a plunger positioned in the mouth of the cup, the plunger having a surface exposed to the cavity, the plunger surface exposed to the cavity having a diffuse reflectance at 580 nanometers of more than twenty percent.

9. The sample cup of claim 8, wherein the plunger surface exposed to the cavity has a diffuse reflectance at 580 nanometers of more than forty percent.

10. The sample cup of claim 9, wherein the plunger surface exposed to the cavity has a diffuse reflectance at 580 nanometers of more than sixty percent.

11. The sample cup of claim 10, wherein the plunger surface exposed to the cavity has a diffuse reflectance at 580 nanometers of more than eighty percent.

12. The sample cup of claim 11, wherein the plunger surface exposed to the cavity has a diffuse reflectance at 580 nanometers of more than ninety percent.

13. The sample cup of claim 11, wherein the plunger is also opaque.

14. The sample cup of claim 13, wherein the plunger is made of TEFLON brand PTFE and the bottom is made of flat optical glass.

* * * * *